(12) United States Patent
Xiao et al.

(10) Patent No.: US 7,468,459 B2
(45) Date of Patent: Dec. 23, 2008

(54) PROCESS FOR THE PREPARATION OF CHIRAL BETA AMINO ACID DERIVATIVES BY ASYMMETRIC HYDROGENATION

(75) Inventors: Yi Xiao, Fanwood, NJ (US); Joseph D. Armstrong, III, Westfield, NJ (US); Shane W. Krska, New Providence, NJ (US); Eugenia Njolito, Princeton, NJ (US); Nelo R. Rivera, New Milford, NJ (US); Yongkui Sun, Bridgewater, NJ (US); Thorsten Rosner, North Plainfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 380 days.

(21) Appl. No.: 10/549,425

(22) PCT Filed: Mar. 15, 2004

(86) PCT No.: PCT/US2004/007793

§ 371 (c)(1),
(2), (4) Date: Sep. 15, 2005

(87) PCT Pub. No.: WO2004/085378

PCT Pub. Date: Oct. 7, 2004

(65) Prior Publication Data

US 2006/0194977 A1 Aug. 31, 2006

Related U.S. Application Data

(60) Provisional application No. 60/455,932, filed on Mar. 19, 2003.

(51) Int. Cl.
*C07C 211/00* (2006.01)
*C07D 249/00* (2006.01)

(52) U.S. Cl. ............... 564/336; 564/337; 548/262.4

(58) Field of Classification Search ............... None
See application file for complete search history.

(56) References Cited

U.S. PATENT DOCUMENTS

| 5,563,309 A | * | 10/1996 | Togni et al. | ........... 585/277 |
| 6,258,979 B1 | * | 7/2001 | Kagan et al. | ........... 562/450 |
| 6,492,544 B2 | | 12/2002 | Krimmer et al. | |
| 6,699,871 B2 | | 3/2004 | Edmondson et al. | |
| 2004/0023344 A1 | | 2/2004 | Matsumura et al. | |

FOREIGN PATENT DOCUMENTS

| EP | 1 103 536 | 5/2001 |
| EP | 1 386 901 | 2/2004 |
| WO | WO 03/004498 | 1/2003 |
| WO | WO 2005/097733 A1 | 10/2005 |

OTHER PUBLICATIONS

Zhu, et al., "Highly efficient Asymmetric Synthesis of β-Amino Acid Derivatives via Rhodium-Catalyzed Hydrogenation of β-(Acylamino)acrylates",*J. Org. Chem*, vol. 64, pp. 6907-6910 (1999).

Lubell, et al., "Enantioselective Synthesis of β-Amino Acids based in BINAP-Ruthenium(II) Catalyzed Hydrogenation", *Tetrahedron Asymmetry*, vol. 2, No. 7, pp. 543-554 (1991).

Hsiao, et al., "Highly Efficient Synthesis of β-Amino Acid Derivatives via Asymmetric Hydrogenation of Unprotected Enamines", *J. Am. Chem. Soc.*, vol. 126, pp. 9918-9919 (2004).

Hayashi, et al. "Asymmetric Synthesis Catalyzed by Chiral Ferrocenylphosphine-Transition Metal Complexes. I. Preparation of Chiral Ferrocenylphosphines", *Bull. Chem. Soc. Jpn.*, vol. 53, pp. 1138-1151 (1980).

* cited by examiner

*Primary Examiner*—Karl J Puttlitz
(74) *Attorney, Agent, or Firm*—Philippe L. Durette; Catherine D. Fitch

(57) ABSTRACT

The present invention relates to a process for the efficient preparation of enantiomerically enriched beta amino acid derivatives which are useful in the asymmetric synthesis of biologically active molecules. The process comprises an enantioselective hydrogenation of a prochiral beta amino acrylic acid derivative substrate in the presence of a transition metal precursor complexed with a chiral ferrocenyl diphosphine ligand.

22 Claims, No Drawings

PROCESS FOR THE PREPARATION OF CHIRAL BETA AMINO ACID DERIVATIVES BY ASYMMETRIC HYDROGENATION

CROSS REFERENCE TO RELATED APPLICATIONS

This application is the National Stage of International Application No. PCT/US04/007793, filed 15 Mar. 2004, which claims the benefit under 35 U.S.C. 119(e) of U.S. Provisional Application No. 60/455,932 filed 19 Mar. 2003.

FIELD OF THE INVENTION

The present invention relates to a process for the efficient preparation of enantiomerically enriched beta amino acid derivatives which are useful in the asymmetric synthesis of biologically active molecules. The process comprises an enantioselective hydrogenation of a prochiral beta-amino acrylic acid derivative substrate in the presence of a transition metal precursor complexed with a chiral ferrocenyl diphosphine ligand.

BACKGROUND OF THE INVENTION

The present invention provides an efficient process for the preparation of an enantiomerically enriched beta amino acid derivative of structural formula I:

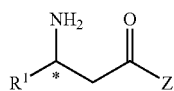

(I)

having the (R)- or (S)-configuration at the stereogenic center marked with an *; wherein Z is $OR^2$, $SR^2$, or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, and $NC_{1-4}$ alkyl, said heterocyclic ring system being optionally fused with a 5- to 6-membered saturated or aromatic carbocyclic ring system or a 5- to 6-membered saturated or aromatic heterocyclic ring system containing one to two heteroatoms selected from O, S, and $NC_{1-4}$ alkyl, said fused ring system being unsubstituted or substituted with one to two substituents independently selected from hydroxy, amino, fluoro, $C_{1-4}$ alkyl, $C_{1-4}$ alkoxy, and trifluoromethyl.

The process of the present invention relates to a method for the preparation of chiral beta amino acid derivatives of structural formula I in an efficient enantioselective fashion via transition metal-catalyzed asymmetric hydrogenation of a prochiral enamine of structural formula II:

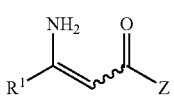

(II)

wherein the amino group is unprotected, in the presence of a chiral ferrocenyl diphosphine ligand.

Methods for asymmetrically reducing enamine carbon-carbon double bonds (C=C—N) using chiral ferrocenyl diphosphines as ligands complexed to a rhodium or iridium precursor have been described in the patent literature (See U.S. Pat. No. 5,563,309 issued Oct. 8, 1996 to Ciba-Geigy Corp. and the related family of patents and patent applications). A related approach to N-acylated beta amino acids using a rhodium Me-DuPHOS catalytic complex has also published (U.S. 2002/0128509 published on Sep. 12, 2002 assigned to Degussa AG). The following publications also describe the asymmetric hydrogenation of N-acylated beta-amino acrylic acids with rhodium metal precursors complexed to a chiral phosphine ligand: (1) T. Hayashi, et al., *Bull. Chem. Soc. Japan*, 53: 1136-1151 (1980); (2) G. Zhu et al., *J. Org. Chem.*, 64: 6907-6910 (1999); and (3) W. D. Lubell, et al., *Tetrahedron: Asymmetry*, 2: 543-554 (1991). In these publications all the examples provided have the amino group in the beta amino acrylic acid derivative substrate protected as an acetamide derivative. The requirement for amine protection introduces two additional chemical steps into the sequence, namely protection and deprotection, and the synthesis of the protected substrate may also be difficult. The process of the present invention circumvents the need for protecting the primary amino group in the substrate for the asymmetric hydrogenation reaction and proceeds with excellent reactivity and enantioselectivity.

SUMMARY OF THE INVENTION

The present invention is concerned with a process for the preparation of enantiomerically enriched beta amino acid derivatives of structural formula I. The process utilizes an asymmetric hydrogenation of a prochiral beta amino acrylic acid derivative, wherein the primary amino group is unprotected, in the presence of a transition metal precursor complexed with a chiral ferrocenyl diphosphine ligand. The process of the present invention is applicable to the preparation of beta amino acid derivatives on a pilot plant or industrial scale. The beta amino acids are useful to prepare a wide variety of biologically active molecules.

DETAILED DESCRIPTION OF THE INVENTION

The present invention provides an efficient process for the preparation of an enantiomerically enriched beta amino acid derivative of structural formula I:

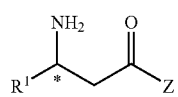

(I)

having the (R)- or (S)-configuration at the stereogenic center marked with an *; in an enantiomeric excess of at least 70% over the opposite enantiomer, wherein Z is $OR^2$, $SR^2$, or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, NH, and $NC_{1-4}$ alkyl, said heterocyclic ring being unsubstituted or substituted with one to three substituents independently selected from oxo, hydroxy, halogen, $C_{1-4}$ alkoxy, and $C_{1-4}$ alkyl wherein alkyl and alkoxy are unsubstituted or substituted with one to five fluorines; and said heterocyclic ring system being optionally fused with a 5- to 6-membered saturated or aromatic carbocyclic ring system or a 5- to 6-membered saturated or aromatic heterocyclic ring system containing one to two heteroatoms selected from O, S, and $NC_{0-4}$ alkyl, said fused ring system being unsubstituted or substituted with one to two substituents selected from hydroxy, amino, fluorine, $C_{1-4}$ alkyl, $C_{1-4}$ alkoxy, and trifluoromethyl.

The process of the present invention comprises the step of hydrogenating a prochiral enamine of structural formula II:

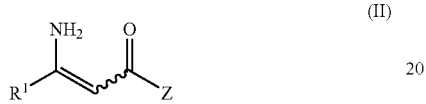

in a suitable organic solvent in the presence of a transition metal precursor complexed to a chiral ferrocenyl diphosphine ligand of structural formula III:

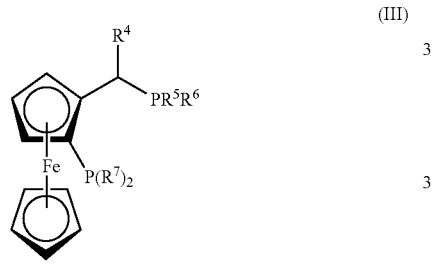

wherein $R^4$ is $C_{1-4}$ alkyl or aryl;
$R^5$ and $R^6$ are each independently $C_{1-6}$ alkyl, $C_{5-12}$ cycloalkyl, or aryl; and
$R^7$ is $C_{1-4}$ alkyl or unsubstituted phenyl.

The process of the present invention contemplates that the catalytic complex of the transition metal precursor and the chiral ferrocenyl diphosphine ligand may be either (a) generated in situ by the sequential or contemporaneous addition of the transition metal species and the chiral ferrocenyl diphosphine ligand to the reaction mixture or (b) pre-formed with or without isolation and then added to the reaction mixture. A pre-formed catalytic complex is represented by the formula:

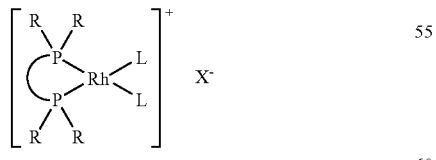

where X represents a non-coordinating anion, such as trifluoromethanesulfonate, tetrafluoroborate, and hexafluorophosphate, and L is a neutral ligand such as an olefin (or chelating di-olefin such as 1,5-cyclooctadiene or norbornadiene) or a solvent molecule (such as MeOH and TFE). In the case where olefin is arene, the complex is represented by the formula:

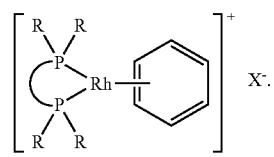

The pre-formed catalytic complex in the case where X represents halogen is represented by the formula:

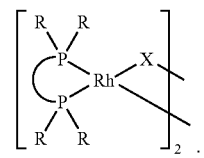

The ligands of structural formula III are known in the art as Josiphos ligands and are commercially available from Solvias AG, Basel, Switzerland.

In one embodiment of the ligands of formula III useful in the process of the present invention, the carbon stereogenic center marked with an ** has the (R)-configuration as depicted in formula IV:

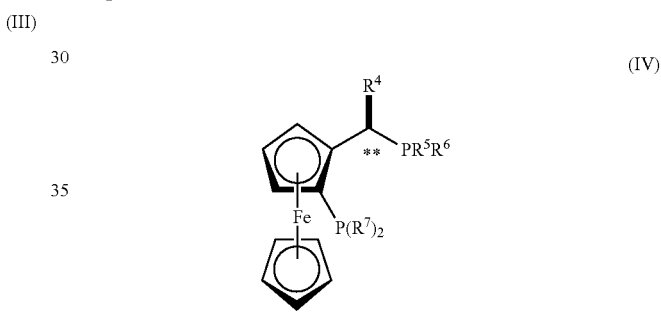

In another embodiment of the ligands of formula II useful in the process of the present invention, $R^4$ is $C_{1-2}$ alkyl, $R^5$ and $R^6$ are $C_{1-4}$ alkyl, and $R^7$ is unsubstituted phenyl. In a class of this embodiment, $R^4$ is methyl, $R^5$ and $R^6$ are t-butyl, and $R^7$ is unsubstituted phenyl. The latter ligand is known in the art as t-butyl Josiphos. Commercially available forms of the t-butyl Josiphos ligand are the S,R and R,S enantiomeric forms. R,S-t-butyl Josiphos is {(R)-1-[(S)-(diphenylphosphino)ferrocenyl]}ethyl-di-tert-butylphosphine of formula V below:

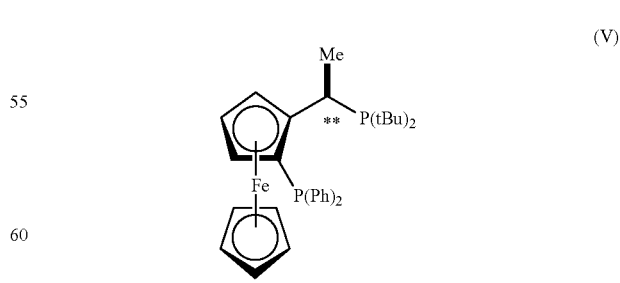

The ferrocenyl diphosphine ligands of formula III have two centers of asymmetry, and the process of the present invention is intended to encompass the use of single enantiomers, individual diastereomers, and mixtures of diastereomers thereof.

The present invention is meant to comprehend the use of all such isomeric forms of the ligands of structural formula III for the asymmetric hydrogenation of a compound of formula II. The facial enantioselectivity of the hydrogenation reaction will depend on the particular stereoisomer of the ligand that is employed in the reaction. It is possible to control the configuration at the newly formed stereogenic center in a compound of formula I marked with an * by the judicious choice of the chirality of the ferrocenyl diphosphine ligand of formula III.

In one embodiment of the substrate for the process of the present invention, $R^1$ is benzyl wherein the phenyl group of benzyl is unsubstituted or substituted one to three substituents selected from the group consisting of fluorine, trifluoromethyl, and trifluoromethoxy. In another embodiment of the process of the present invention, Z is $OR^2$ or $NR^2R^3$. In a class of this embodiment, $NR^2R^3$ is a heterocycle of the structural formula VI:

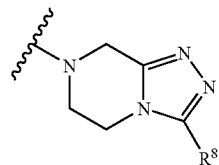

(VI)

wherein $R^8$ is hydrogen or $C_{1-4}$ alkyl which is unsubstituted or substituted with one to five fluorines. In another class of this embodiment, Z is $OR^2$.

In another embodiment of the substrate for the process of the present invention, $R^1$ is 6-methoxy-pyridin-3-yl and Z is $C_{1-4}$ alkoxy. In a class of this embodiment, Z is methoxy or ethoxy.

The asymmetric hydrogenation reaction of the present invention is carried out in a suitable organic solvent. Suitable organic solvents include lower alkanols, such as methanol, ethanol, isopropyl alcohol, hexafluoroisopropyl alcohol, phenol, 2,2,2-trifluoroethanol SE), and mixtures thereof; tetrahydrofuran; methyl t-butyl ether; and mixtures thereof.

The reaction temperature for the reaction may be in the range of about 10° C. to about 90° C. A preferred temperature range for the reaction is about 45° C. to about 65° C.

The hydrogenation reaction can be performed at a hydrogen pressure range of about 20 psig to about 1500 psig. A preferred hydrogen pressure range is about 80 psig to about 200 psig.

The transition metal precursor is [M(monoolefin)$_2$Cl]$_2$, [M(diolefin)Cl]$_2$, [M(monoolefin)$_2$acetylacetonate], [M(diolefin)acetylacetonate], [M(monoolefin)$_4$]X, or [M(diolefin)$_2$]X wherein X is a non-coordinating anion selected from the group consisting of methanesulfonate, trifluoromethanesulfonate (Tf), tetrafluoroborate (BF$_4$), hexafluorophosphate (PF$_6$), and hexafluoroantimonate (SbF$_6$), and M is rhodium (Rh) or iridium (Ir). Transition metal precursors where M is ruthenium (Ru) are [M(arene)Cl$_2$]$_2$, [M(diolefin)Cl$_2$]$_n$, or [M(diolefin)(η3-2-methyl-1-propenyl)$_2$]. In one embodiment the transition metal precursor is [Rh(cod)Cl]$_2$, [Rh(norbornadiene)Cl]$_2$, [Rh(cod)$_2$]X, or [Rh(norbornadiene)$_2$]X. In a class of this embodiment, the transition metal precursor is [Rh(cod)Cl]$_2$.

The ratio of transition metal precursor to substrate is about 0.01 to about 10 mol %. A preferred ratio of the transition metal precursor to substrate is about 0.05 mol % to about 0.4 mol %.

The beta amino acrylic acid derivative substrates of formula II for the asymmetric hydrogenation contain an olefinic double bond, and unless specified otherwise, are meant to include both E and Z geometric isomers or mixtures thereof as starting materials. The squiggly bond in the substrate of structural formula II signifies either the Z or E geometric isomer or a mixture thereof.

In one embodiment of the present invention, the geometric configuration of the double bond in the beta amino acrylic acid derivative substrate for the asymmetric hydrogenation reaction is the Z-configuration as depicted in formula VII:

(VII)

The beta amino acrylate esters of formula II (Z=$OR^2$ or $SR^2$) for the asymmetric hydrogenation reaction of the present invention can be prepared from a beta-keto ester of structural formula VI in high yield by reaction with a source of ammonia in a suitable organic solvent such as methanol, ethanol, isopropyl alcohol, tetrahydrofuran, and aqueous mixtures thereof.

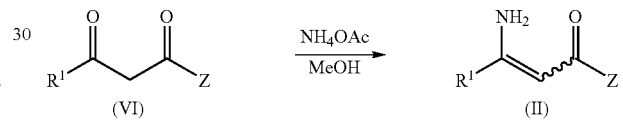

Sources of ammonia include ammonium acetate, ammonium hydroxide, and ammonium formate. In one embodiment the source of ammonia is ammonium acetate. The beta-keto esters can be prepared as described by D. W. Brooks et al., *Angew. Chem. Int. Ed. Engl.,* 18: 72 (1979).

The beta amino acrylamides can be prepared from the corresponding esters via amide exchange as described in *Org. Syn. Collect.,* Vol. 3, p. 108.

Another embodiment of the present invention concerns a process for the preparation of a compound of structural formula 1:

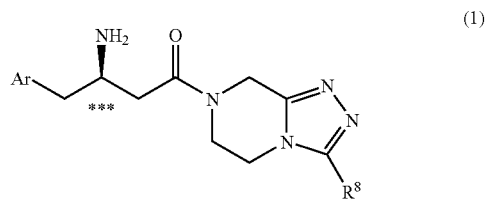

(1)

having the (R)-configuration at the stereogenic center marked with an ***;

in an enantiomeric excess of at least 70% over the enantiomer having the opposite (S)-configuration, wherein Ar is phenyl which is unsubstituted or substituted with one to five substituents independently selected from the group consisting of fluorine, trifluoromethyl, and trifluoromethoxy; and $R^8$ is hydrogen or $C_{1-4}$ alkyl unsubstituted or substituted with one to five fluorines; comprising the steps of:

(a) producing a compound of structural formula 2:

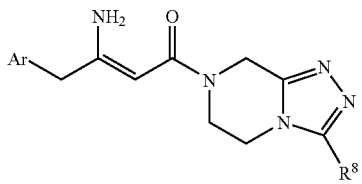

(2)

by treating a compound of structural formula 3:

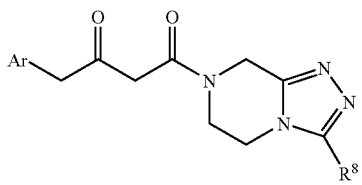

(3)

with a source of ammonia in a suitable organic solvent; and (b) hydrogenating a compound of structural formula 2:

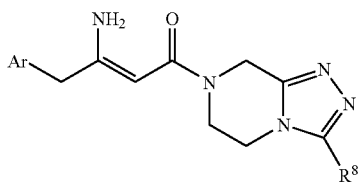

(2)

in a suitable organic solvent in the presence of a rhodium metal precursor and a chiral ferrocenyl disphosphine of structural formula IV:

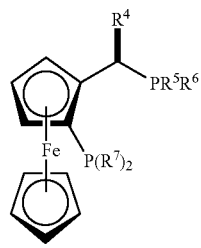

(IV)

wherein $R^4$ is $C_{1-4}$ alkyl or aryl;
$R^5$ and $R^6$ are each independently $C_{1-6}$ alkyl, $C_{5-12}$ cycloalkyl, or aryl; and
$R^7$ is $C_{1-4}$ alkyl or unsubstituted phenyl.

In a class of this embodiment, Ar is 2,5-difluorophenyl or 2,4,5-trifluorophenyl. In a subclass of this class, $R^8$ is trifluoromethyl.

In another class of this embodiment, the rhodium metal precursor is chloro(1,5-cyclooctadiene)rhodium(I) dimer {[Rh(cod)Cl]₂}.

In another class of this embodiment, $R^4$ is methyl, $R^5$ and $R^6$ are both t-butyl, and $R^7$ is unsubstituted phenyl. In a subclass of this class, the rhodium metal precursor is chloro(1,5-cyclooctadiene)rhodium(I) dimer.

In yet another class of this embodiment, $R^4$ is methyl, $R^5$ and $R^6$ are both t-butyl, $R^7$ is unsubstituted phenyl, Ar is 2,5-difluorophenyl or 2,4,5-trifluorophenyl, $R^8$ is trifluoromethyl, and the rhodium metal precursor is chloro(1,5-cyclooctadiene)rhodium(I) dimer.

In another embodiment the compound of structural formula 1 is obtained with an enantiomeric excess of greater than 90%. In a class of this embodiment the compound of structural formula 1 is obtained with an enantiomeric excess of greater than 95%.

Compounds of structural formula 1 are disclosed in WO 03/004498 (published 16 Jan. 2003) as inhibitors of dipeptidyl peptidase-IV which are useful for the treatment of Type 2 diabetes.

A further embodiment of the present invention comprises structurally novel intermediates of structural formula 2 which are useful in the preparation of compounds of structural formula 1:

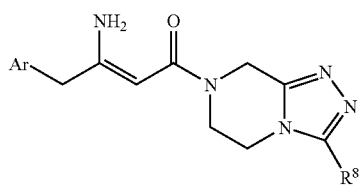

(2)

wherein Ar is phenyl which is unsubstituted or substituted with one to five substituents independently selected from the group consisting of fluorine, trifluoromethyl, and trifluoromethoxy; and $R^8$ is hydrogen or $C_{1-4}$ alkyl unsubstituted or substituted with one to five fluorines.

In a class of this embodiment of novel intermediates of formula 2, Ar is 2,5-difluorophenyl or 2,4,5-trifluorophenyl and $R^8$ is trifluoromethyl.

Throughout the instant application, the following terms have the indicated meanings:

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

The process of the present invention provides compounds of structural formula I with high optical purity, typically in excess of 70% ee. In one embodiment, compounds of formula I are obtained with an optical purity in excess of 80% ee. In a class of this embodiment, compounds of formula I are obtained with an optical purity in excess of 90% ee. In a subclass of this class, compounds of formula I are obtained with an optical purity in excess of 95% ee.

The term "enantioselective" shall mean a reaction in which one enantiomer is produced (or destroyed) more rapidly than the other, resulting in the predominance of the favored enantiomer in the mixture of products.

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like. The alkyl groups are unsubstituted or substituted with one to three groups independently selected from the group consisting of halogen, hydroxy, carboxy, aminocarbonyl, amino, $C_{1-4}$ alkoxy, and $C_{1-4}$ alkylthio.

The term "cycloalkyl" is intended to mean cyclic rings of alkanes of five to twelve total carbon atoms, or any number within this range (i.e., cyclopentyl, cyclohexyl, cycloheptyl, etc).

The term "halogen" is intended to include the halogen atoms fluorine, chlorine, bromine, and iodine.

The abbreviation "cod" means "1,5-cyclooctadiene."

The term "aryl" includes phenyl and naphthyl. "Aryl" is unsubstituted or substituted with one to five substituents independently selected from fluoro, hydroxy, trifluoromethyl, amino, $C_{1-4}$ alkyl, and $C_{1-4}$ alkoxy.

The term "arene" refers to benzene, naphthalene, and o-, m-, or p-isopropyltoluene (o, m, or p-cymene).

The term "olefin" refers to a acyclic or cyclic hydrocarbon containing one or more double bonds including aromatic cyclic hydrocarbons. The term includes, but is not limited to, 1,5-cyclooctadiene and norbornadiene ("nbd").

The term "heteroaryl" means a 5- or 6-membered aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include, but are not limited to, pyrrolyl, isoxazolyl, isothiazolyl, pyrazolyl, pyridinyl, oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, and dibenzofuranyl. "Heteroaryl" is unsubstituted or substituted with one to five substituents independently selected from fluoro, hydroxy, trifluoromethyl, amino, $C_{1-4}$ alkyl, and $C_{1-4}$ alkoxy.

Representative experimental procedures utilizing the novel process are detailed below. The following Examples are for the purposes of illustration only and are not intended to limit the process of the present invention to the specific conditions for making these particular compounds.

EXAMPLE 1

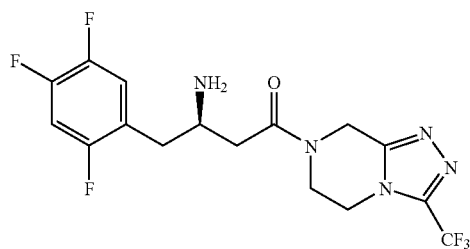

(2R)-4-oxo-4-[3-(trifluoromethyl)-5,6-dihydro[1,2,4] triazolo[4,3-α]pyrazin-7(8H)-yl]-1-(2,4,5-trifluorophenyl)butan-2-amine (2-5)

Preparation of 3-(trifluoromethyl)-5,6,7,8-tetrahydro [1,2,4]triazolo[4,3-α]pyrazine, hydrochloride salt (1-4)

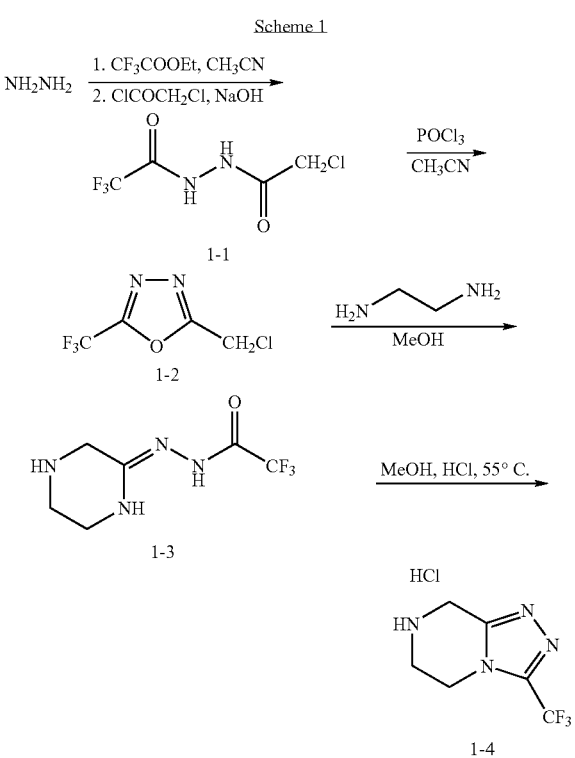

Step A: Preparation of bishydrazide (1-1)

Hydrazine (20.1 g, 35 wt % in water, 0.22 mol) was mixed with 310 mL of acetonitrile. 31.5 g of ethyl trifluoroacetate (0.22 mol) was added over 60 min. The internal temperature was increased to 25° C. from 14° C. The resulting solution was aged at 22-25° C. for 60 min. The solution was cooled to 7° C. 17.9 g of 50 wt % aqueous NaOH (0.22 mol) and 25.3 g of chloroacetyl chloride (0.22 mol) were added simultaneously over 130 min at a temperature below 16° C. When the reaction was complete, the mixture was vacuum distilled to remove water and ethanol at 27~30° C. and under 26~27 in Hg vacuum. During the distillation, 720 mL of acetonitrile was added slowly to maintain constant volume (approximately 500 mL). The slurry was filtered to remove sodium chloride. The cake was rinsed with about 100 mL of acetonitrile. Removal of the solvent afforded bis-hydrazide 1-1 (43.2 g, 96.5% yield, 94.4 area % pure by HPLC assay).

$^1$H-NMR (400 M, DMSO-d$_6$): δ 4.2 (s, 2H), 10.7 (s, 1H), and 11.6 (s, 1H) ppm. $^{13}$C-NMR (100 Mz, DMSO-d$_6$): δ 41.0, 116.1 (q, J=362 Hz), 155.8 (q, J=50 Hz), and 165.4 ppm.

Step B: Preparation of 5-(trifluoromethyl)-2-(chloromethyl)-1,3,4-oxadiazole (1-2)

Bishydrazide 1-1 from Step A (43.2 g, 0.21 mol) in ACN (82 mL) was cooled to 5° C. Phosphorus oxychloride (32.2 g, 0.21 mol) was added, maintaining the temperature below 10° C. The mixture was heated to 80° C. and aged at this temperature for 24 h until HPLC showed less than 2 area % of 1-1. In a separate vessel, 260 mL of IPAc and 250 mL of water were mixed and cooled to 0° C. The reaction slurry was charged to the quench keeping the internal temperature below 10° C. After the addition, the mixture was agitated vigorously for 30 min, the temperature was increased to room temperature and the aqueous layer was cut. The organic layer was then washed with 215 mL of water, 215 mL of 5 wt % aqueous sodium bicarbonate and finally 215 mL of 20 wt % aqueous brine solution. BPLC assay yield after work up was 86-92%. Volatiles were removed by distillation at 75-80 mm Hg, 55° C. to afford an oil which could be used directly in Step C without further purification. Otherwise the product can be purified by distillation to afford 1-2 in 70-80% yield.

$^1$H-NMR (400 MHz, CDCl$_3$): δ 4.8 (s, 2H) ppm. $^{13}$C-NMR (100 MHz, CDCl$_3$): δ 32.1, 115.8 (q, J=337 Hz), 156.2 (q, J=50 Hz), and 164.4 ppm.

Step C: Preparation of N-[(2Z)-piperazin-2-ylidene] trifluoroacetohydrazide (1-3)

To a solution of ethylenediamine (33.1 g, 0.55 mol) in methanol (150 mL) cooled at −20° C. was added distilled oxadiazole 1-2 from Step B (29.8 g, 0.16 mol) while keeping the internal temperature at −20° C. After the addition was complete, the resulting slurry was aged at −20° C. for 1 h. Ethanol (225 mL) was then charged and the slurry slowly warmed to −5° C. After 60 min at −5° C., the slurry was filtered and washed with ethanol (60 mL) at −5° C. Amidine 1-3 was obtained as a white solid in 72% yield (24.4 g, 99.5 area wt % pure by HPLC).

$^1$H-NMR (400 MHz, DMSO-d$_6$): δ 2.9 (t, 2H), 3.2 (t, 2H), 3.6 (s, 2H), and 8.3 (b, 1H) ppm. $^{13}$C-NMR (100 MHz, DMSO-d$_6$): δ 40.8, 42.0, 43.3, 119.3 (q, J=350 Hz), 154.2, and 156.2 (q, J=38 Hz) ppm.

Step D: Preparation of 3-(trifluoromethyl)-5,6,7,8-tetrahydro[1,2,4]triazolo[4,3-α]pyrazine, hydrochloride salt (1-4)

A suspension of amidine 1-3 (27.3 g, 0.13 mol) in 110 mL of methanol was warmed to 55° C. 37% Hydrochloric acid (11.2 mL, 0.14 mol) was added over 15 min at this temperature. During the addition, all solids dissolved resulting in a clear solution. The reaction was aged for 30 min. The solution was cooled down to 20° C. and aged at this temperature until a seed bed formed (10 min to 1 h). 300 mL of MTBE was charged at 20° C. over 1 h. The resulting slurry was cooled to 2° C., aged for 30 min and filtered. Solids were washed with 50 mL of ethanol:MTBE (1:3) and dried under vacuum at 45° C. Yield of triazole 1-4 was 26.7 g (99.5 area wt % pure by HPLC).

$^1$H-NMR (400 MHz, DMSO-d$_6$): δ 3.6 (t, 2H), 4.4 (t, 2H), 4.6 (s, 2H), and 10.6 (b, 2H) ppm; $^{13}$C-NMR (100 MHz, DMSO-d$_6$): δ: 39.4, 39.6, 41.0, 118.6 (q, J=325 Hz), 142.9 (q, J=50 Hz), and 148.8 ppm.

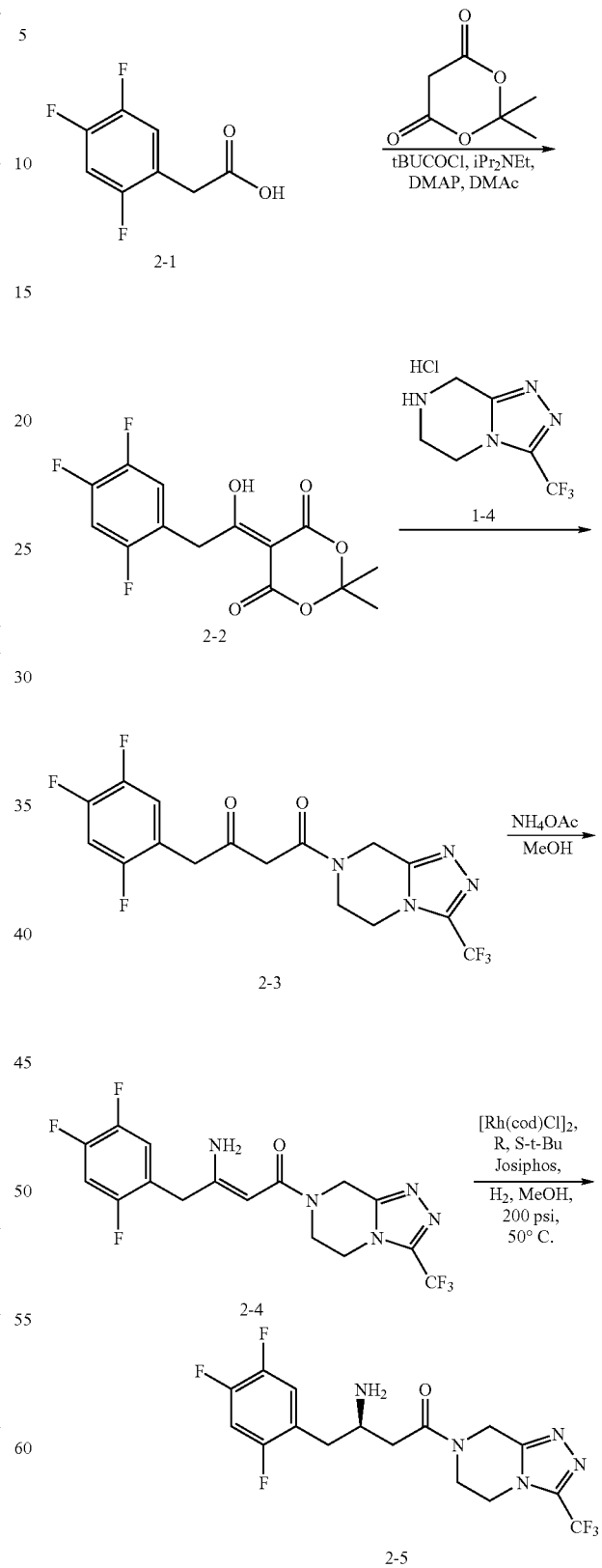

Step A: Preparation of 4-oxo-4-[3-(trifluoromethyl)-5,6-dihydro[1,2,4]triazolo[4,3-α]pyrazin-7(8H)-yl]-1-(2,4,5-trifluorophenyl)butan-2-one (2-3)

2,4,5-Trifluorophenylacetic acid (2-1) (150 g, 0.789 mol), Meldrum's acid (125 g, 0.868 mol), and 4-(dimethylamino)pyridine (DMAP) (7.7 g, 0063 mol) were charged into a 5 L three-neck flask. N,N-Dimethylacetamide (DMAc) (525 mL) was added in one portion at room temperature to dissolve the solids. N,N-diisopropylethylamine (282 mL, 1.62 mol) was added in one portion at room temperature while maintaining the temperature below 40° C. Pivaloyl chloride (107 mL, 0.868 mol) was added dropwise over 1 to 2 h while maintaining the temperature between 0 and 5° C. The reaction mixture was aged at 5° C. for 1 h. Triazole hydrochloride 1-4 (180 g, 0.789 mol) was added in one portion at 40-50° C. The reaction solution was aged at 70° C. for several h. 5% Aqueous sodium hydrogencarbonate solution (625 mL) was then added dropwise at 20-45° C. The batch was seeded and aged at 20-30° C. for 1-2 h. Then an additional 525 mL of 5% aqueous sodium hydrogencarbonate solution was added dropwise over 2-3 h. After aging several h at room temperature, the slurry was cooled to 0-5° C. and aged 1 h before filtering the solid. The wet cake was displacement-washed with 20% aqueous DMAc (300 mL), followed by an additional two batches of 20% aqueous DMAc (400 mL), and finally water (400 mL). The cake was suction-dried at room temperature. The isolated yield of final product 2-3 was 89%.

Step B: Preparation of (2Z)-4-oxo-4-[3-(trifluoromethyl)-5,6-dihydro[1,2,4]triazolo[4,3-α]pyrazin-7(8H)-yl]-1-(2,4,5-trifluorophenyl)but-2-en-2-amine (2-4)

A 5 L round-bottom flask was charged with methanol (100 mL), the ketoamide 2-3 (200 g), and ammonium acetate (110.4 g). Methanol (180 mL) and 28% aqueous ammonium hydroxide (58.6 ml) were then added keeping the temperature below 30° C. during the addition. Additional methanol (100 mL) was added to the reaction mixture. The mixture was heated at reflux temperature and aged for 2 h. The reaction was cooled to room temperature and then to about 5° C. in an ice-bath. After 30 min, the solid was filtered and dried to afford 2-4 as a solid (180 g); m.p. 271.2° C.

Step C: Preparation of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (2-5)

Into a 500 ml flask were charged chloro(1,5-cyclooctadiene)rhodium(I) dimer {[Rh(cod)Cl]$_2$} (292 mg, 0.59 mmol) and (R,S) t-butyl Josiphos (708 mg, 1.31 mmol) under a nitrogen atmosphere. Degassed MeOH was then added (200 mL) and the mixture was stirred at room temperature for 1 h. Into a 4 L hydrogenator was charged the enamine amide 2-4 (118 g, 0.29 mol) along with MeOH (1 L). The slurry was degassed. The catalyst solution was then transferred to the hydrogenator under nitrogen. After degassing three times, the enamine amide was hydrogenated under 200 psi hydrogen gas at 50° C. for 13 h.

Assay yield was determined by HPLC to be 93% and optical purity to be 94% ee.

The optical purity was further enhanced in the following manner. The methanol solution from the hydrogenation reaction (18 g in 180 mL MeOH) was concentrated and switched to methyl t-butyl ether (MTBE) (45 mL). Into this solution was added aqueous H$_3$PO$_4$ solution (0.5 M, 95 mL). After separation of the layers, 3N NaOH (35 mL) was added to the water layer, which was then extracted with MTBE (180 mL+100 mL). The MTBE solution was concentrated and solvent switched to hot toluene (180 mL, about 75° C.). The hot toluene solution was then allowed to cool to 0° C. slowly (5-10 h). The crystals were isolated by filtration (13 g, yield 72%, 98-99% ee); m.p. 114.1-115.7° C.

$^1$H NMR (300 MHz, CD$_3$CN): δ 7.26 (m), 7.08 (m), 4.90 (s), 4.89 (s), 4.14 (m), 3.95 (m), 3.40 (m), 2.68 (m), 2.49 (m), 1.40 (bs).

Compound 2-5 exists as amide bond rotamers. Unless indicated, the major and minor rotamers are grouped together since the carbon-13 signals are not well resolved:

$^{13}$C NMR (CD$_3$CN): δ 171.8, 157.4 (ddd, $J_{CF}$=242.4, 9.2, 2.5 Hz), 152.2 (major), 151.8 (minor), 149.3 (ddd; $J_{CF}$=246.7, 14.2, 12.9 Hz), 147.4 (ddd, $J_{CF}$=241.2, 12.3, 3.7 Hz), 144.2 (q, $J_{CF}$=38.8 Hz), 124.6 (ddd, $J_{CF}$=18.5, 5.9, 4.0 Hz), 120.4 (dd, $J_{CF}$=19.1, 6.2 Hz), 119.8 (q, $J_{CF}$=268.9 Hz), 106.2 (dd, $J_{CF}$=29.5, 20.9 Hz), 50.1, 44.8, 44.3 (minor), 43.2 (minor), 42.4, 41.6 (minor), 41.4, 39.6, 38.5 (minor), 36.9.

The following high-performance liquid chromatographic (HPLC) conditions were used to determine percent conversion to product:
Column: Waters Symmetry C18, 250 mm×4.6 mm
Eluent: Solvent A: 0.1 vol % HClO$_4$/H$_2$O
  Solvent B: acetonitrile
Gradient: 0 min 75% A: 25% B
  10 min 25% A: 75% B
  12.5 min 25% A: 75% B
  15 min 75% A: 25% B
Flow rate: 1 mL/min
Injection Vol.: 10 µL
UV detection: 210 nm
Column temp.: 40° C.
Retention times: compound 2-4: 9.1 min
  compound 2-5: 5.4 min
  tBu Josiphos: 8.7 min The following high-performance liquid chromatographic (HPLC) conditions were used to determine optical purity:
Column: Chirapak, AD-H, 250 mm×4.6 mm
Eluent: Solvent A: 0.2 vol. % diethylamine in heptane
  Solvent B: 0.1 vol % diethylamine in ethanol
Isochratic Run Time: 18 min
Flow rate: 0.7 mL/min
Injection Vol.: 7 µL
UV detection: 268 nm
Column temp.: 35° C.
Retention times: (R)-amine 2-5: 13.8 min
  (S)-amine: 11.2 min

EXAMPLE 2

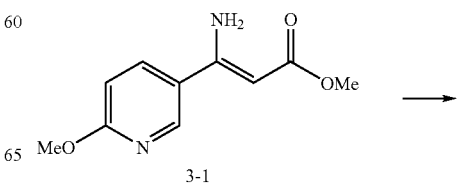

3-1

-continued

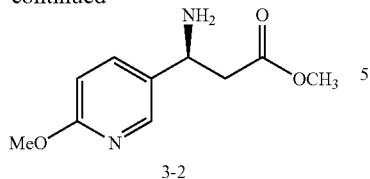

Methyl(3S)-3-amino-3-(6-methoxypyridin-3-yl)propanoate (3-2)

Into a 7 in L vial were charged chloro(1,5-cyclooctadiene) rhodium(I) dimer {[Rh(cod)Cl]$_2$} (14.2 mg, 0.029 mmol) and (R,S)-t-Bu Josiphos (31.3 mg, 0.058 mmol) under a nitrogen atmosphere. Degassed methanol (1 mL) was then added and the catalytic complex was stirred for 45 min at room temperature. In a separate 2-mL vial, the enamine ester 3-1 (0.1 g, 0.5 mmol) was dissolved in 0.9 mL distilled 2,2,2-trifluoroethanol. To the same vial 0.1 mL of the prepared catalyst solution was added resulting in 1 mol % catalyst loading and a 2,2,2-trifluoroethanol/methanol mixture of 90/10. The hydrogenation vial was then sealed and transferred into the hydrogenation bomb under nitrogen. After degassing three times with hydrogen, the enamine ester was hydrogenated under 90-psig-hydrogen gas at 50° C. for 13.5 h. Assay yield was determined by HPLC to be 88% and optical purity to be 89% ee.

$^1$H-NMR (400 Mz, CDCl$_3$): δ 1.81 (bs, 2H), 2.64 (m, 2H), 3.68 (s, 3H), 3.91 (s, 3H), 4.4 (dd, 1H), 6.72 (d, 1H), 7.62 (dd, 1H), and 8.11 (s, 1H) ppm.

EXAMPLES 3-6

TABLE$^a$

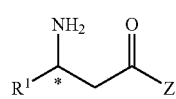

| Ex. | R$^1$ | % yield$^b$ | % ee$^c$ | config. |
|---|---|---|---|---|
| 3 | Ph | 75 | 96 | S |
| 4 | 4-F-Ph | 74 | 96 | S |
| 5 | 4-OMe-Ph | 82 | 96 | S |
| 6 | PhCH$_2$— | 94 | 97 | S |

$^a$Reaction conditions: 0.15 mol % [Rh(cod)Cl]$_2$; 0.333 mol % (R,S)-t-Bu Josiphos, 50° C., 100 psig H$_2$.
$^b$Assay yield;
$^c$Assayed by chiral HPLC using a AS-RH or AD-RH chiral column eluting with 25-40% acetonitrile/water as the mobile phase.

What is claimed is:

1. A process for preparing a compound of structural formula I:

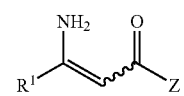

(I)

having the (R)- or (S)-configuration at the stereogenic center marked with an *; in an enantiomeric excess of at least 70% over the opposite enantiomer, wherein Z is OR$^2$, SR$^2$, or NR$^2$R$^3$;
R$^1$ is C$_{1-8}$ alkyl, aryl, heteroaryl, aryl-C$_{1-2}$ alkyl, or heteroaryl-C$_{1-2}$ alkyl;
R$^2$ and R$^3$ are each independently hydrogen, C$_{1-8}$ alkyl, aryl, or aryl-C$_{1-2}$ alkyl; or R$^2$ and R$^3$ together with the nitrogen atom to which they are attached form a 4- to 7-membered heterocyclic ring system optionally containing an additional heteroatom selected from O, S, NH, and NC$_{1-4}$ alkyl, said heterocyclic ring being unsubstituted or substituted with one to three substituents independently selected from oxo, hydroxy, halogen, C$_{1-4}$ alkoxy, and C$_{1-4}$ alkyl wherein alkyl and alkoxy are unsubstituted or substituted with one to five fluorines; and said heterocyclic ring system being optionally fused with a 5- to 6-membered saturated or aromatic carbocyclic ring system or a 5- to 6-membered saturated or aromatic heterocyclic ring system containing one to two heteroatoms selected from O, S, and NC$_{0-4}$ alkyl, said fused ring system being unsubstituted or substituted with one to two substituents selected from hydroxy, amino, fluorine, C$_{1-4}$ alkyl, C$_{1-4}$ alkoxy, and trifluoromethyl;
comprising the step of hydrogenating a prochiral enamine of structural formula II:

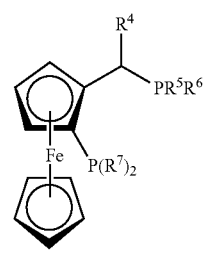

(II)

in a suitable organic solvent in the presence of a transition metal precursor complexed to a chiral ferrocenyl diphosphine ligand of structural formula III:

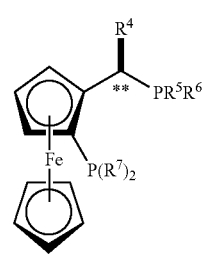

(III)

wherein R$^4$ is C$_{1-4}$ alkyl or aryl;
R$^5$ and R$^6$ are each independently C$_{1-6}$ alkyl, C$_{5-12}$ cycloalkyl, or aryl; and
R$^7$ is C$_{1-4}$ alkyl or unsubstituted phenyl.

2. The process of claim 1 wherein said ferrocenyl diphosphine ligand is of structural formula IV:

(IV)

wherein the stereogenic center marked with an ** has the (R)-configuration.

3. The process of claim 2 wherein $R^4$ is $C_{1-2}$ alkyl, $R^5$ and $R^6$ are $C_{1-4}$ alkyl, and $R^7$ is unsubstituted phenyl.

4. The process of claim 3 wherein $R^4$ is methyl, $R^5$ and $R^6$ are t-butyl, and $R^7$ is unsubstituted phenyl.

5. The process of claim 1 wherein $R^1$ is benzyl wherein the phenyl group of benzyl is unsubstituted or substituted one to three substituents selected from the group consisting of fluorine, trifluoromethyl, and trifluoromethoxy.

6. The process of claim 1 wherein Z is $OR^2$ or $NR^2R^3$.

7. The process of claim 6 wherein $NR^2R^3$ is a heterocycle of the structural formula VI:

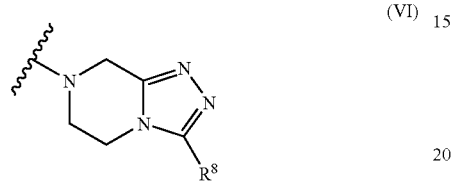

(VI)

wherein $R^8$ is hydrogen or $C_{1-4}$ alkyl which is unsubstituted or substituted with one to five fluorines.

8. The process of claim 1 wherein said transition metal precursor is $[M(cod)Cl]_2$, $[M(norbornadiene)Cl]_2$, $[M(cod)_2]X$, or $[M(norbornadiene)_2]X$ wherein X is methanesulfonate, trifluoromethanesulfonate, tetrafluoroborate, hexafluorophosphate, or hexafluoroantimonate and M is rhodium or iridium.

9. The process of claim 8 wherein said transition metal precursor is $[Rh(cod)Cl]_2$.

10. A process for preparing a compound of structural formula 1:

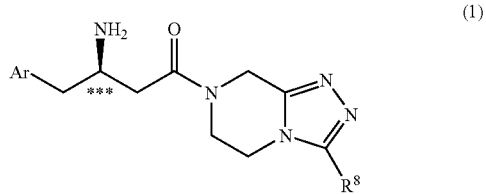

(1)

having the (R)-configuration at the stereogenic center marked with an ***;
in an enantiomeric excess of at least 70% over the enantiomer having the opposite (S)-configuration; wherein
Ar is phenyl which is unsubstituted or substituted with one to five substituents independently selected from the group consisting of fluorine, trifluoromethyl, and trifluoromethoxy; and
$R^8$ is hydrogen or $C_{1-4}$ alkyl unsubstituted or substituted with one to five fluorines;
comprising the step of:
hydrogenating a compound of structural formula 2:

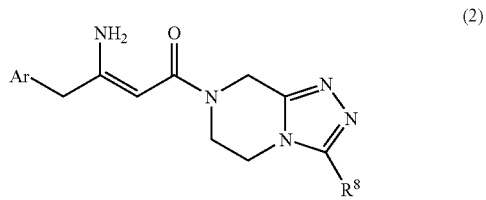

(2)

in a suitable organic solvent in the presence of a rhodium metal precursor and a chiral ferrocenyl disphosphine of structural formula IV:

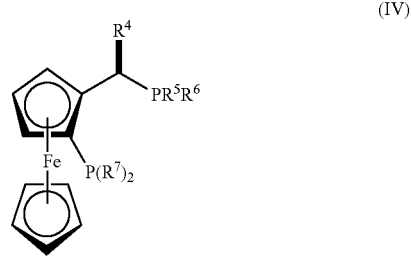

(IV)

wherein $R^4$ is $C_{1-4}$ alkyl or aryl;
$R^5$ and $R^6$ are each independently $C_{1-6}$ alkyl, $C_{5-12}$ cycloalkyl, or aryl; and
$R^7$ is $C_{1-4}$ alkyl or unsubstituted phenyl.

11. The process of claim 10 additionally comprising the step of producing a compound of structural formula 2:

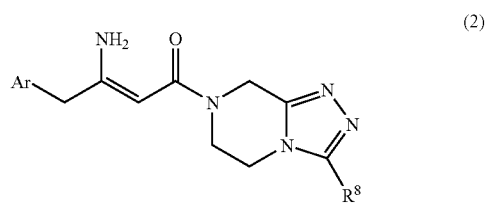

(2)

by treating a compound of structural formula 3:

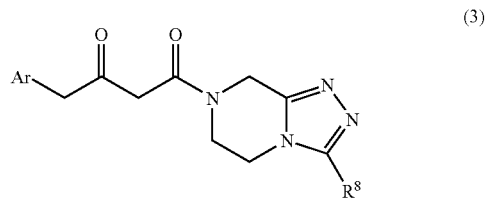

(3)

with a source of ammonia in a suitable organic solvent.

12. The process of claim 10 wherein Ar is 2,5-difluorophenyl or 2,4,5-trifluorophenyl and $R^8$ is trifluoromethyl.

13. The process of claim 10 wherein said rhodium metal precursor is $[Rh(cod)Cl]_2$.

14. The process of claim 10 wherein $R^4$ is methyl, $R^5$ and $R^6$ are both t-butyl, and $R^7$ is unsubstituted phenyl.

15. The process of claim 14 wherein said rhodium metal precursor is $[Rh(cod)Cl]_2$.

16. The process of claim 10 wherein $R^4$ is methyl, $R^5$ and $R^6$ are both t-butyl, $R^7$ is unsubstituted phenyl, Ar is 2,5-difluorophenyl or 2,4,5-trifluorophenyl, $R^8$ is trifluoromethyl, and the rhodium metal precursor is chloro(1,5-cyclooctadiene)rhodium(I) dimer.

17. The process of claim 11 wherein said source of ammonia is ammonium acetate.

18. A process for preparing a compound of structural formula 1:

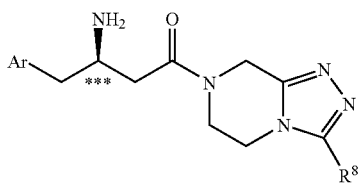

having the (R)-configuration at the stereogenic center marked with an ***;
in an enantiomeric excess of at least 70% over the enantiomer having the opposite (S)-configuration; wherein
Ar is phenyl which is unsubstituted or substituted with one to five substituents independently selected from the group consisting of fluorine, trifluoromethyl, and trifluoromethoxy; and
$R^8$ is hydrogen or $C_{1-4}$ alkyl unsubstituted or substituted with one to five fluorines;
comprising the steps of:
(a) producing a compound of structural formula 2:

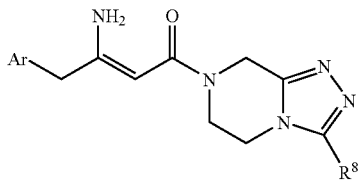

by treating a compound of structural formula 3:

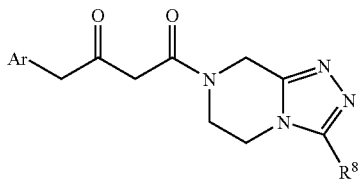

with a source of ammonia in a suitable organic solvent; and
(b) hydrogenating a compound of structural formula 2:

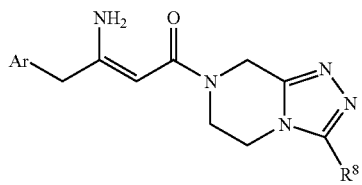

in a suitable organic solvent in the presence of a rhodium metal precursor and a chiral ferrocenyl disphosphine of structural formula IV:

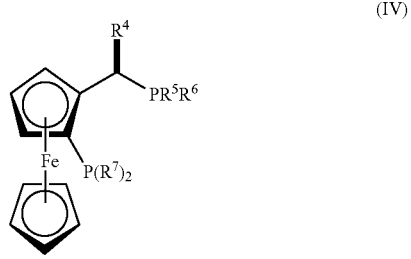

wherein $R^4$ is $C_{1-4}$ alkyl or aryl;
$R^5$ and $R^6$ are each independently $C_{1-6}$ alkyl, $C_{5-12}$ cycloalkyl, or aryl; and
$R^7$ is $C_{1-4}$ alkyl or unsubstituted phenyl.

19. The process of claim 2 wherein Z is $OR^2$.

20. The process of claim 19 wherein $R^1$ is 6-methoxy-pyridin-3-yl and Z is $C_{1-4}$ alkoxy.

21. The process of claim 20 wherein Z is methoxy or ethoxy.

22. The process of claim 21 wherein $R^4$ is methyl, $R^5$ and $R^6$ are t-butyl, $R^7$ is phenyl, and said transition metal precursor is $[Rh(cod)Cl]_2$.

* * * * *